United States Patent
Lapointe et al.

(10) Patent No.: US 11,375,894 B2
(45) Date of Patent: Jul. 5, 2022

(54) SPECTROREFLECTOMETRIC SYSTEM PROVIDED WITH A POINTER MODE FOR COMBINED IMAGING AND SPECTRAL ANALYSIS

(71) Applicant: ZILIA INC., Quebec (CA)

(72) Inventors: Nicolas Lapointe, Quebec (CA); Dominic Sauvageau, Quebec (CA)

(73) Assignee: ZILIA INC., Quebec (CA)

( * ) Notice: Subject to any disclaimer, the term of this patent is extended or adjusted under 35 U.S.C. 154(b) by 271 days.

(21) Appl. No.: 16/895,487

(22) Filed: Jun. 8, 2020

(65) Prior Publication Data

US 2020/0297208 A1  Sep. 24, 2020

Related U.S. Application Data

(63) Continuation-in-part of application No. PCT/CA2018/051559, filed on Dec. 5, 2018.

(Continued)

(51) Int. Cl.
*A61B 5/00* (2006.01)
*A61B 3/12* (2006.01)
(Continued)

(52) U.S. Cl.
CPC .............. *A61B 3/12* (2013.01); *A61B 3/0008* (2013.01); *A61B 3/14* (2013.01); *A61B 5/0075* (2013.01); *G01J 3/2823* (2013.01); *G01J 3/447* (2013.01)

(58) Field of Classification Search
CPC .......... A61B 3/12; A61B 3/0008; A61B 3/14; A61B 5/0075; A61B 5/1455; G01J 3/2823; G01J 3/447
See application file for complete search history.

(56) References Cited

U.S. PATENT DOCUMENTS

| 5,308,919 A | 5/1994 | Minnich |
| 5,742,374 A * | 4/1998 | Nanjo ................. A61B 3/145 |
| | | 351/221 |

(Continued)

FOREIGN PATENT DOCUMENTS

| WO | 03/009750 A2 | 2/2003 |
| WO | 2018/112660 A1 | 6/2018 |

OTHER PUBLICATIONS

De Kock et al., "Reflectance Pulse Oximetry Measurements from the Retinal Fundus," IEEE Transactions on Biomedical Engineering, vol. 40, No. 8, Aug. 31, 1993, pp. 817-823.

(Continued)

*Primary Examiner* — Jonathan M Hansen
(74) *Attorney, Agent, or Firm* — Workman Nydegger

(57) ABSTRACT

A spectroreflectometric system for performing a spectral analysis on the fundus of a patient's eye or other medium is provided. The system includes an imaging device and a spectral analyser. Illumination light from an illumination light source is projected towards the fundus of the patient's eye. The resulting light from the fundus is separated by a beam splitter into an imaging portion travelling along an imaging light path to reach the imaging device and a spectral analysis portion deviated to a spectral analysis light path. The system further includes a pointer light source optically coupled to the spectral analysis light path. The system is operable in an acquisition mode to concurrently obtain an image of the fundus of the patient's eye and a spectral analysis of an analysis spot on this fundus, and in a pointer mode to obtain a visual representation of the analysis spot within the image.

20 Claims, 10 Drawing Sheets

Related U.S. Application Data

(60) Provisional application No. 62/672,916, filed on May 17, 2018, provisional application No. 62/595,260, filed on Dec. 6, 2017.

(51) Int. Cl.
    *A61B 3/00*     (2006.01)
    *A61B 3/14*     (2006.01)
    *G01J 3/447*     (2006.01)
    *G01J 3/28*     (2006.01)

(56) References Cited

U.S. PATENT DOCUMENTS

| | | |
|---|---|---|
| 5,919,132 A | 7/1999 | Faubert et al. |
| 6,069,690 A * | 5/2000 | Xu .......................... G01J 3/44 356/73 |
| 6,149,589 A | 11/2000 | Diaconu et al. |
| 2018/0367786 A1* | 12/2018 | Furst .................. H04N 5/2256 |
| 2020/0397286 A1* | 12/2020 | Ralston ................ A61B 3/10 |

OTHER PUBLICATIONS

Extended European Search Report from corresponding European Application No. EP18885321.2, dated Jul. 14, 2021.
International Search Report and Written Opinion from PCT Application No. PCT/CA2018/051559, dated Mar. 7, 2019.

\* cited by examiner

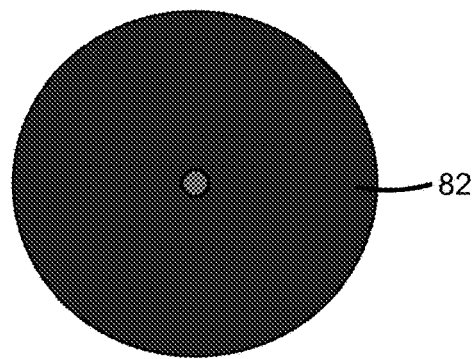
FIG. 5A
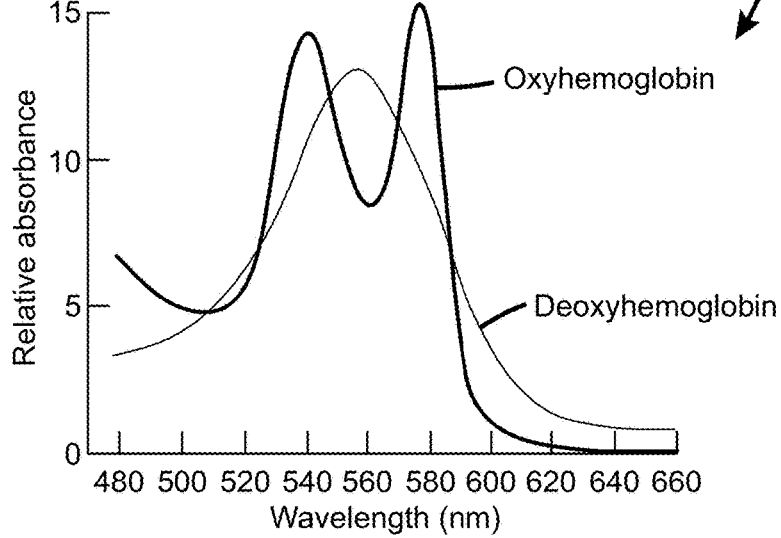
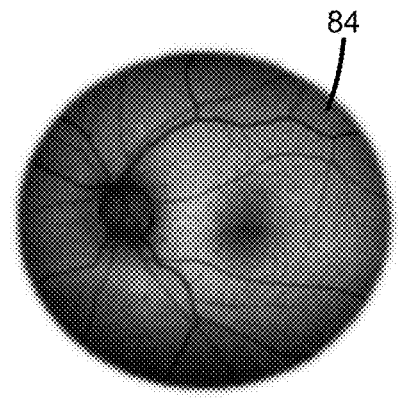
FIG. 5B
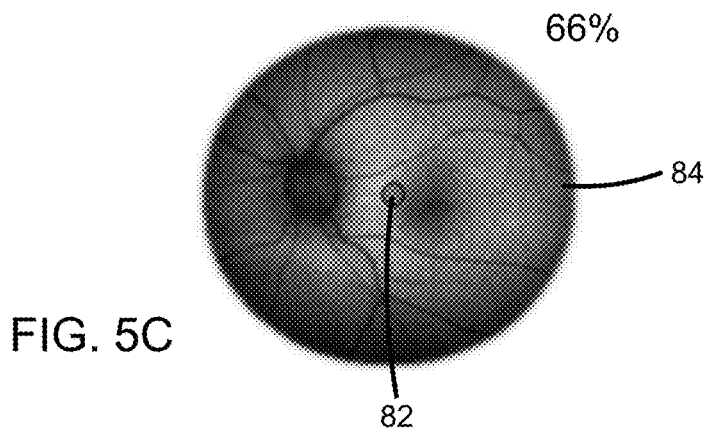
FIG. 5C

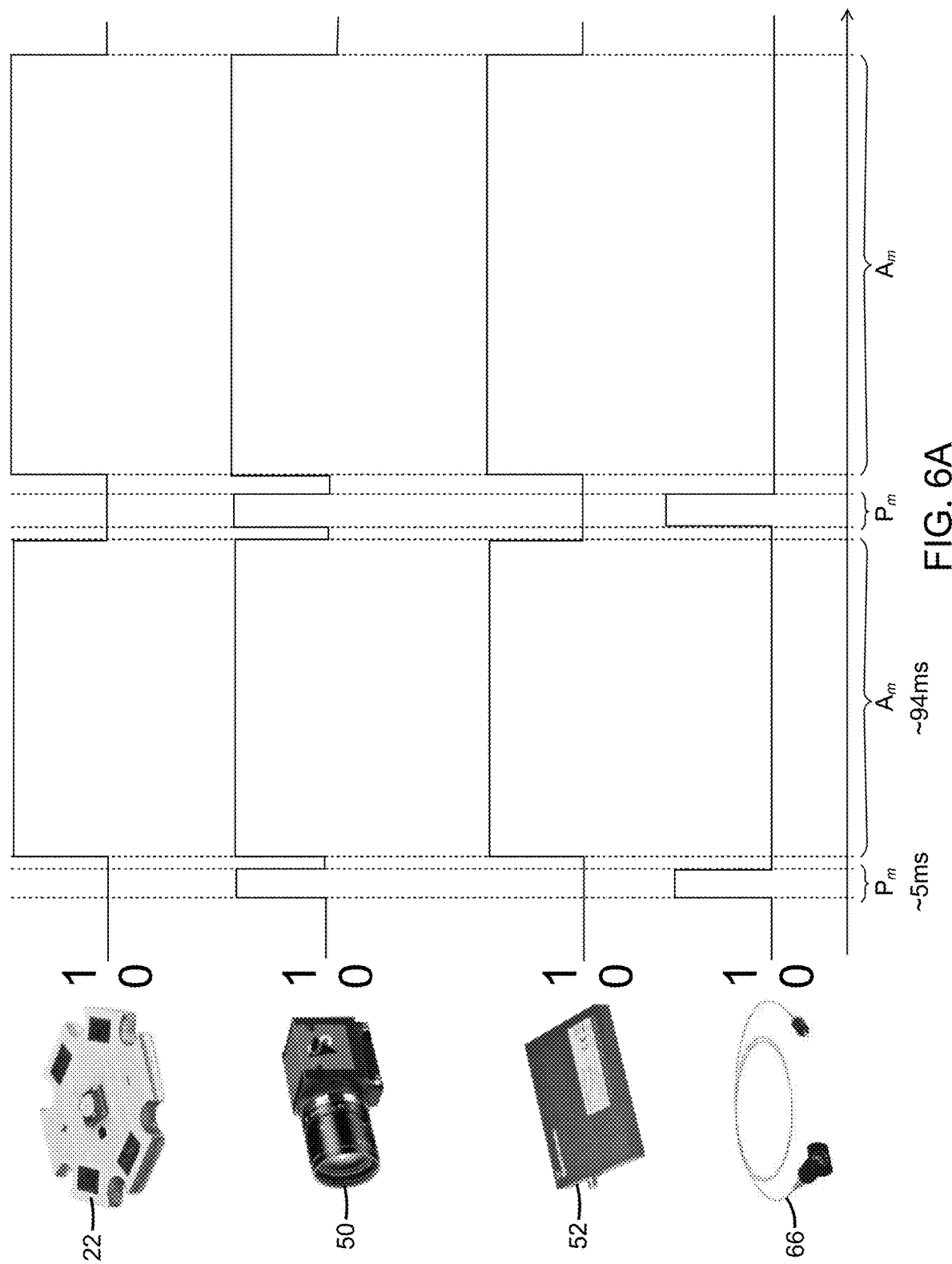

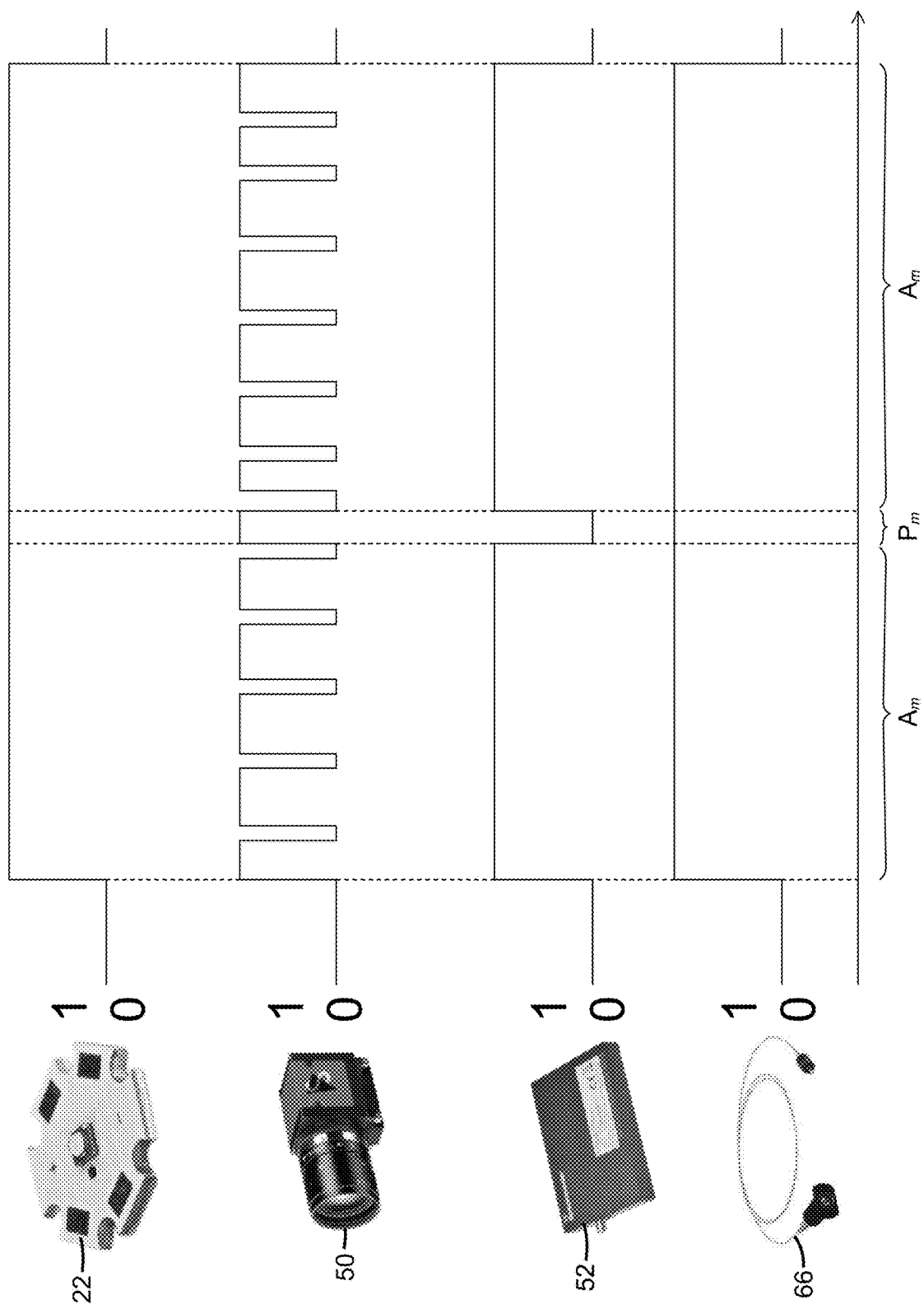

SPECTROREFLECTOMETRIC SYSTEM PROVIDED WITH A POINTER MODE FOR COMBINED IMAGING AND SPECTRAL ANALYSIS

TECHNICAL FIELD

The technical field generally relates to devices for oximetry or other eye-related measurements and more particularly concerns a spectroreflectometric system and method providing both a spectral analysis and a visual representation of an analysis spot within the fundus of a patient's eye.

BACKGROUND

Ocular oximetry, that is, the measurement of the degree of oxygen saturation of blood in tissues of the eye, is a useful non-invasive tool with widespread medical and health monitoring applications. Indeed, measurement of oxygen saturation in biological tissues can provide valuable information on metabolism, responses to stress, the pathophysiology of different illnesses and conditions or the efficacy of administered treatments.

Spectroreflectometric systems can be used to provide oximetric measurements or other information from the fundus of a patient's eye through a spectral analysis of light resulting from the interaction of illumination light with the fundus medium or features in the eye fundus. For optimal use in the field, oximeters or equivalent devices and systems should preferably be efficient, simple to use and easy to manufacture, low cost and miniaturisation of such equipment are also factors of interest. A challenge in providing such features is in the proper design of the optical arrangement for image and data acquisition and signal redirection for analysis. Such a design should provide proper targeting and identification of the analysis spot whose interaction with light is being analysed spectrally.

There remains a need for an improved device that can be used for ocular oximetry or the analysis of other parameters in a patient's eye that provide at least some of the above-mentioned advantages.

SUMMARY

In accordance with one aspect, there is provided a spectroreflectometric system for performing a spectral analysis on the fundus of a patient's eye, comprising:
  an imaging device;
  a spectral analyser;
  an optical assembly defining an imaging light path between the patient's eye and the imaging device and a spectral analysis light path between the patient's eye and the spectral analyser; and
  a pointer light source operable to generate a pointer light beam and optically coupled to the spectral analysis light path such that said pointer light beam is projectable on the fundus of the patient's eye at an analysis spot of said spectral analyser.

In some implementations, the optical assembly may include a beamsplitter positioned along the imaging light path and configured to direct an imaging portion of light travelling along the imaging light path to the imaging device and a spectral analysis portion of said light to the spectral analysis light path. The beamsplitter may be a dichroic beamsplitter. In one example, the dichroic beamsplitter may have a transmission spectral profile defining:
  one or more high transmissivity regions associated with a spectrum of the imaging portion of light travelling along the imaging light path;
  a low transmissivity region associated with a spectrum of the spectral analysis portion of the light travelling along the imaging light path; and
  a partial transmissivity region associated with a spectrum of the pointer light beam.

In other examples, the beamsplitter may be configured to divide the light travelling along the imaging light path into the imaging portion and the spectral analysis portion according to intensity ratios, or polarisation directions.

In some implementations, the optical assembly comprises:
  a first optical fiber link extending between the spectral analysis light path and the spectral analyser;
  a second optical fiber link extending between the spectral analysis light path and the pointer light source; and
  a three-prong coupler optically coupling the spectral analysis light path, the first optical fiber link and the second optical fiber link.

The three-prong coupler may for example comprise a multimode optical circulator, a double-clad optical fiber or a free-space beamsplitting configuration.

In some implementations, the optical assembly comprises an illumination subassembly configured to project illumination light towards the fundus of the patient's eye. The spectroreflectometric system may further include an illumination light source operable to generate the illumination light and optically coupled to the illumination subassembly. In some implementations, the illumination subassembly comprises:
  a holed mirror positioned at an angle along the imaging light path between the patient's eye and the beamsplitter, the holed mirror having a central hole aligned with the imaging light path; and
  beam shaping optics projecting the illumination light from illumination light source onto the holed mirror for reflection towards the fundus of the patient's eye.

The beam shaping optics of the illumination subassembly may comprise a screen blocking a center of the illumination beam and optically aligned with the central hole of the holed mirror.

In some implementations, the spectroreflectometric system may further comprising a controller configured to operate in:
  an acquisition mode wherein the controller operates the imaging device and spectral analyser to concurrently obtain an image of the fundus of the patient's eye and a spectral analysis of the analysis spot on said fundus; and
  a pointer mode wherein the controller operates the pointer light source and imaging device to obtain a visual representation of the analysis spot within said image.

In some implementations, the spectroreflectometric system further comprises a spot shifting mechanism positioned in the spectral analysis light path and configured to shift a position of the analysis spot over said fundus of the patient's eye. The spot shifting mechanism may comprise shift optics comprising at least one steerable mirror for changing the incidence angle between the spectral imaging light path and the beamsplitter.

In accordance with one aspect, there is provided a spectroreflectometric system for performing a spectral analysis on the fundus of a patient's eye.

The spectroreflectometric system may include an imaging device, a spectral analyser, and an illumination light source controllable to generate illumination light.

The spectroreflectometric system further includes an optical assembly defining an imaging light path between the patient's eye and the imaging device and a spectral analysis light path between the imaging light path and the spectral analyser. The optical assembly includes an illumination subassembly optically coupled to the illumination light source and configured to project the illumination light from said illumination light source towards the fundus of the patient's eye. The optical assembly further includes a beamsplitter positioned along the imaging light path and configured to allow an imaging portion of light travelling along the imaging light path to reach the imaging device, and to divert a spectral analysis portion of said light to the spectral analysis light path.

The spectroreflectometric system further includes a pointer light source optically coupled to the spectral analysis light path and controllable to generate a pointer light beam.

Finally, a controller is provided. The controller is configured to operate in:
an acquisition mode wherein the controller activates the illumination light source, imaging device and spectral analyser to concurrently obtain an image of the fundus of the patient's eye and a spectral analysis of an analysis spot on said fundus; and
a pointer mode wherein the controller activates the pointer light source and imaging device to obtain a visual representation of the analysis spot within said image.

In some implementations, the beamsplitter is a dichroic beamsplitter. The dichroic beamsplitter may have a transmission spectral profile defining:
one or more high transmissivity regions associated with a spectrum of the imaging portion of light travelling along the imaging light path;
a low transmissivity region associated with a spectrum of the spectral analysis portion of the light travelling along the imaging light path; and
a partial transmissivity region associated with a spectrum of the pointer light beam.

The beamsplitter may alternatively be configured to divide the light travelling along the imaging light path into the imaging portion and the spectral analysis portion according to one of intensity ratios and polarisation directions.

In some implementations, the optical assembly comprises:
a first optical fiber link extending between the spectral analysis light path and the spectral analyser;
a second optical fiber link extending between the spectral analysis light path and the pointer light source; and
a three-prong coupler optically coupling the spectral analysis light path, the first optical fiber link and the second optical fiber link.

In some implementations, the spectroreflectometric system may further comprise a spot shifting mechanism positioned in the spectral analysis light path and configured to shift a position of the analysis spot over said fundus of the patient's eye. The spot shifting mechanism may comprise shift optics comprising at least one steerable mirror for changing the incidence angle between the spectral imaging light path and the beamsplitter.

In accordance with another aspect, there is also provided a spectroreflectometric method for performing a spectral analysis on the fundus of a patient's eye. The method includes:
providing a spectroreflectometric system operable in an acquisition mode and a pointer mode;
in the acquisition mode:
illuminating the fundus of the patient's eye, thereby obtaining return light from said fundus, the return light propagating along an imaging light path;
separating, for example using a beamsplitter, the return light into an imaging portion continuing along the imaging light path, and a spectral analysis portion diverted to a spectral analysis light path;
detecting the imaging portion using an imaging device to obtain an image of the fundus of the patient's eye;
detecting the spectral analysis portion using a spectral analyser to obtain a spectral analysis of an analysis spot on said fundus; and
in the pointer mode:
coupling a pointer light beam to the spectral analysis light so that said pointer light beam is projected towards the fundus of the patient's eye and a reflection thereof propagated along the imaging light path to the imaging device;
detecting the reflection of the pointer light beam using the imaging device to obtain a visual representation of the analysis spot within said image.

In accordance with another aspect, there is provided a system for performing a spectral analysis on a medium, comprising:
an imaging device;
a spectral analyser;
an optical assembly defining an imaging light path between the medium and the imaging device and a spectral analysis light path between the medium and the spectral analyser, the optical assembly comprising a beamsplitter positioned along the imaging light path and configured to direct an imaging portion of light travelling along the imaging light path to the imaging device and a spectral analysis portion of said light to the spectral analysis light path;
a pointer light source optically coupled to the spectral analysis light path and operable to generate a pointer light beam; and
a controller configured to operate in:
an acquisition mode wherein the controller operates the imaging device and the spectral analyser to concurrently obtain an image of the medium and a spectral analysis of an analysis spot in said medium; and
a pointer mode wherein the controller operates the pointer light source and imaging device to obtain a visual representation of the analysis spot within said image.

In some implementations, the beamsplitter is a dichroic beamsplitter. The dichroic beamsplitter may have a transmission spectral profile defining:
one or more high transmissivity regions associated with a spectrum of the imaging portion of light travelling along the imaging light path;
a low transmissivity region associated with a spectrum of the spectral analysis portion of the light travelling along the imaging light path; and
a partial transmissivity region associated with a spectrum of the pointer light beam.

In some implementations, the beamsplitter is configured to divide the light travelling along the imaging light path into the imaging portion and the spectral analysis portion according to one of intensity ratios and polarisation directions.

In some implementations, the optical assembly comprises:

a first optical fiber link extending between the spectral analysis light path and the spectral analyser;

a second optical fiber link extending between the spectral analysis light path and the pointer light source; and a three-prong coupler optically coupling the spectral analysis light path, the first optical fiber link and the second optical fiber link.

In some implementations, the three-prong coupler comprises on of a multimode optical circulator, a double-clad optical fiber and a free-space beamsplitting configuration.

In some implementations, the optical assembly comprises an illumination subassembly configured to project illumination light towards the medium.

In some implementations, the system further comprises an illumination light source operable to generate the illumination light and optically coupled to the illumination subassembly.

In some implementations, the illumination subassembly comprises:

a holed mirror positioned at an angle along the imaging light path between the patient's eye and the beamsplitter, the holed mirror having a central hole aligned with the imaging light path; and beam shaping optics projecting the illumination light from illumination light source onto the holed mirror for reflection towards the medium.

In some implementations, the beam shaping optics of the illumination subassembly comprises a screen blocking a center of the illumination beam and optically aligned with the central hole of the holed mirror.

In some implementations, the system further comprises a controller configured to operate in:

an acquisition mode wherein the controller operates the imaging device and spectral analyser to concurrently obtain an image of the medium and a spectral analysis of the analysis spot on said medium; and a pointer mode wherein the controller operates the pointer light source and imaging device to obtain a visual representation of the analysis spot within said image.

In some implementations, the system further comprises a spot shifting mechanism positioned in the spectral analysis light path and configured to shift a position of the analysis spot over said medium. The spot shifting mechanism may comprise shift optics comprising at least one steerable mirror for changing the incidence angle between the spectral imaging light path and the beamsplitter.

Other features and aspects will be better understood upon reading of embodiments thereof with reference to the appended drawings.

BRIEF DESCRIPTION OF THE DRAWINGS

FIG. 5A to FIG. 5C respectively show the visual representation of the analysis spot, the image and corresponding spectral analysis of the fundus of the patient's eye, and the superposed visual representation of the analysis spot over the image of the fundus in one example of implementation.

FIGS. 6A and 6B are timing diagrams of the operation of a system according to some implementation.

DETAILED DESCRIPTION

The present description generally relates to spectroreflectometric systems for performing a spectral analysis on the fundus of a patient's eye.

In the context of the present application, the expression "spectroreflectometric" is generally used as a contraction of the terms "spectral" and "reflectometric" in reference to techniques related to spectral reflectometry. As readily understood by those skilled in the art, reflectometry refers to the use of reflected light or other electromagnetic waves to analyse the properties of a medium. Light is typically projected towards the medium and the interactions of the light wavefront with the medium interface leads to the generation of return light having optical properties affected by the medium. In spectral reflectometry, a spectral analysis of the return light, that is, an analysis of the properties of the return light as a function of its wavelength profile, is used to obtain or deduce information about the medium and its composition.

Spectral reflectometry can be used in ophthalmologic contexts to sense oxygen levels in the fundus of the eye of a patient. By way of example, oxygen levels are assessed through the presence of oxyhemoglobin which has a characteristic light absorbance pattern. Similarly, the concentration of deoxyhemoglobin, and carboxyhemoglobin (related to the levels of carbon dioxide present) can be determined based on their respective light absorbance patterns. These parameters and their regulation are indicative of metabolism, responses to stress and stimuli and, potentially, pathophysiologies. It will however be understood that other molecules and phenomena may also be studied, such as for example fluorescence, inasmuch as they lead to alterations in the spectral profiles of reflected light. It will also be understood that the spectral analysis may be performed for different regions of the fundus of the patient's eye or on features present on the fundus. In other implementations, the spectral analysis may be performed on other portions of the eye such as the conjunctiva.

It will however be readily understood that the system described herein may be used for different applications than for the spectroreflectometric analysis of the eye. More broadly, the system below may be of use in any context where spectral information from a portion of an imaged medium is desired. One skilled in the art will readily understand that in some applications the system may be used to analyze light transmitted or reflected by a medium of interest. The medium under study may be other than the eye such as for example the skin, organ tissues, exposed muscle tissues, and other biological tissues. In some embodiments the medium under study may be an ex-vivo sample such as blood, tissues etc. stored in a transparent container such as a bag, a vial, a syringe or a cuvette, or on a suitable substrate.

Figure 1:
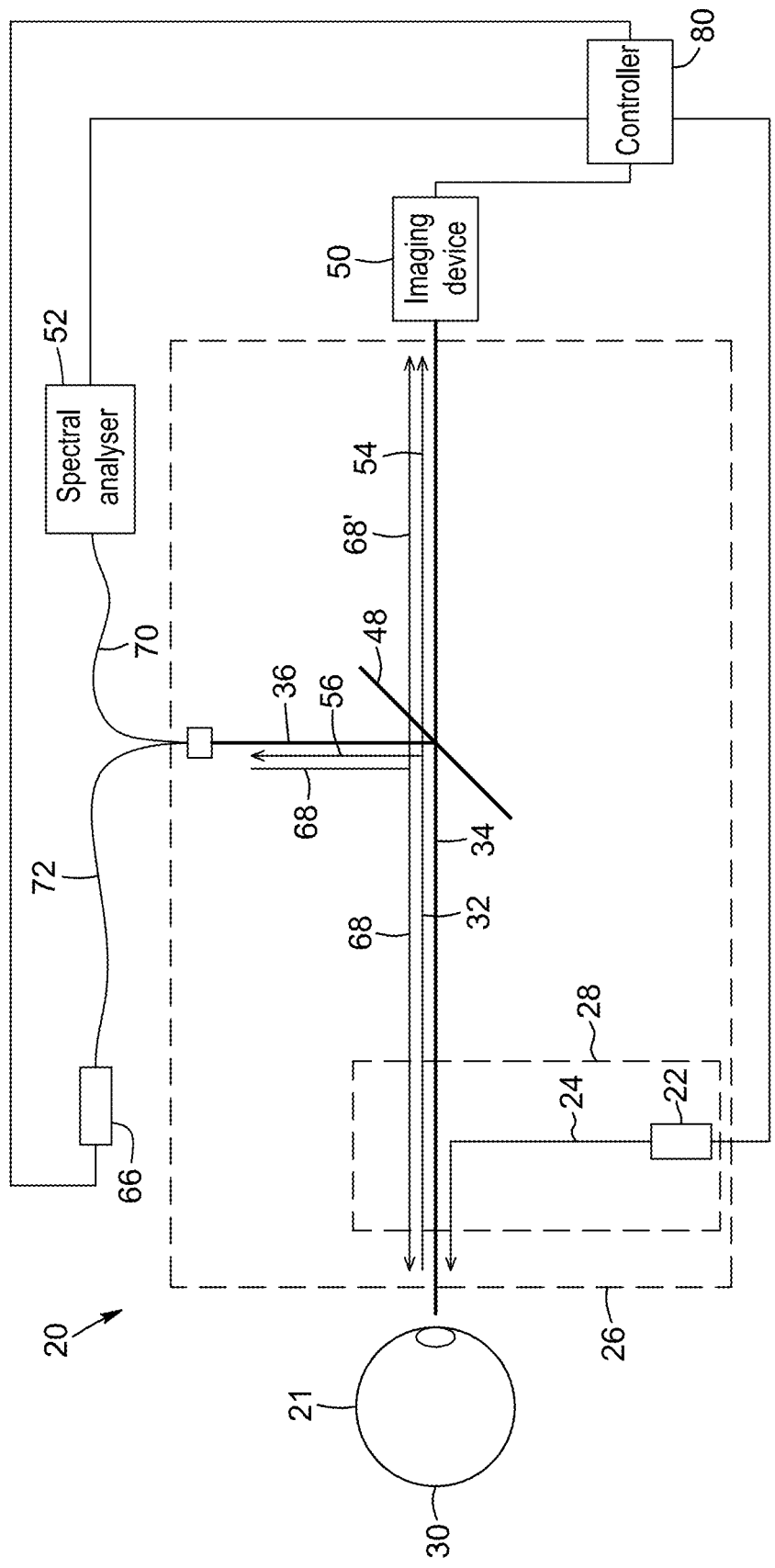
FIG. 1 is a schematic representation of a spectroreflectometric system according to an embodiment.

With reference to FIG. 1, there is shown a high-level schematized representation of a spectroreflectometric system 20 for performing a spectral analysis on the fundus 30 of a patient's eye 21, illustrating a spectroreflectometric method according to one embodiment.

The spectroreflectometric system 20 includes an imaging device 50, a spectral analyser 52 and a pointer light source 66. In this illustrated configuration, the spectroreflectometric system 20 is operable in two modes: an acquisition mode, and a pointer mode.

The spectroreflectometric system 20 further includes an optical assembly defining an imaging light path 34 between the patient's eye 21 and the imaging device 50, and a spectral analysis light path 36 between the patient's eye 21 and the spectral analyser 52. In acquisition mode, the fundus 30 of the patient's eye 21 is illuminated, thereby obtaining return light 32 from the fundus 30 which propagates along the imaging light path 34. The return light 32 is preferably divided into an imaging portion 54 propagating along the imaging light path 32, and a spectral analysis portion 56 diverted to the spectral analysis light path 36. The imaging portion 54 is detected via the imaging device 50 to obtain an image of the fundus 30 of the patient's eye 21. The diverted spectral analysis portion 56 is detected using the spectral analyser 52 to obtain and a spectral analysis of an analysis spot on the fundus 30.

In the pointer mode, the pointer light source 66 generates a pointer light beam 68 which is coupled to the spectral analysis light path 36 such that the pointer light beam 68 is projected on the fundus of the patient's eye 21 at the analysis spot of the spectral analyser.

It will be readily understood that the expression "analysis spot" refers to a region or area on the fundus of the patient's eye or other medium under analysis from which the portion of the return light reaching the spectral analyser originates. The analysis spot may have different sizes and/or shapes mostly determined by the geometry and configuration of the spectroreflectometric system.

Figure 2A:
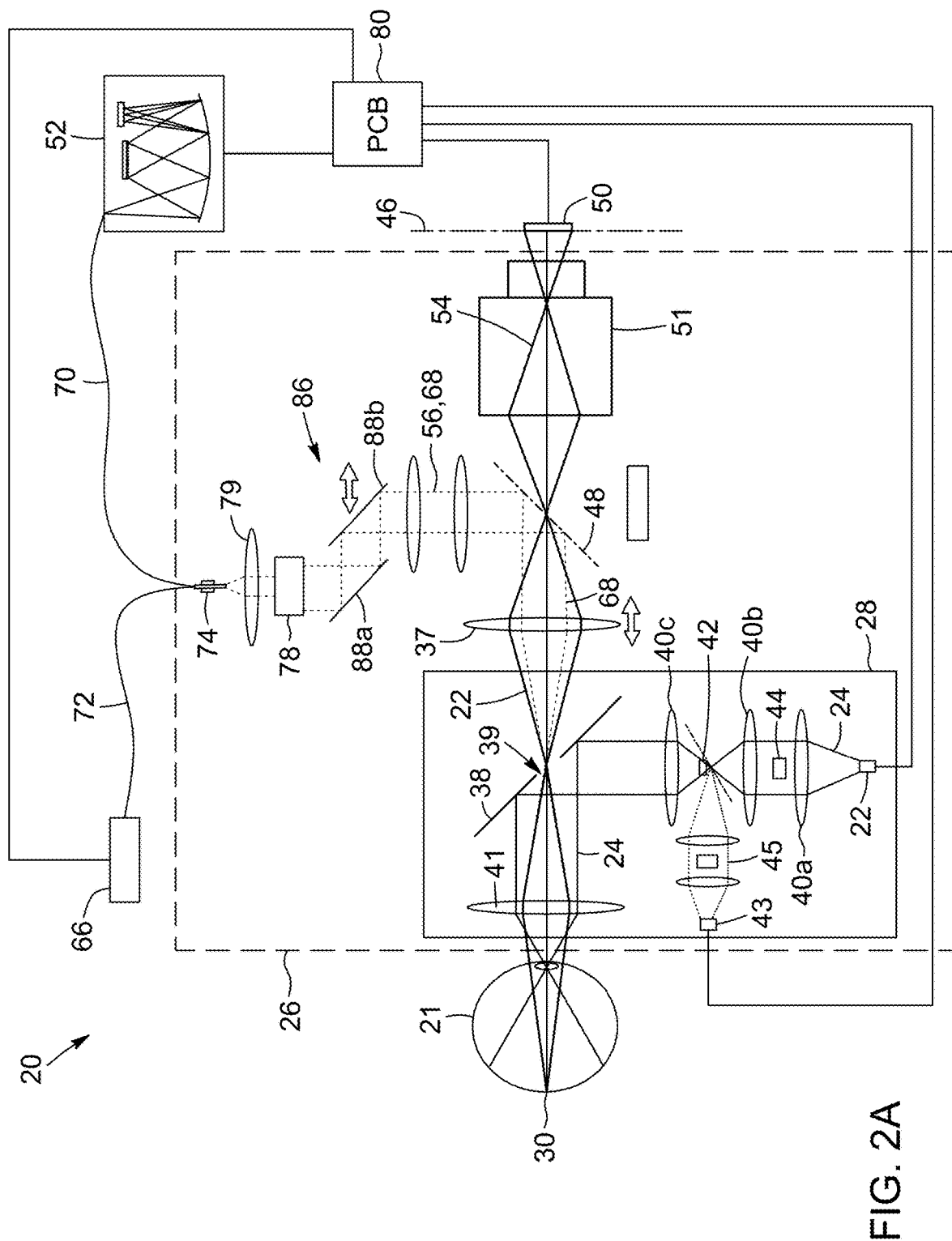
FIG. 2A is a detailed representation of a spectroreflectometric system according to one example of implementation, used to perform a spectral analysis on the fundus of a patient's eye.

Referring to FIG. 2A, a schematized representation of a configuration embodying a spectroreflectometric system 20 according to one example is illustrated.

As mentioned above, the spectroreflectometric system 20 includes an imaging device 50. In some implementations, the imaging device 50 may be embodied by a CCD or CMOS sensor, or any surface that is sensitive and converts light intensity or energy into a useful signal. The imaging device 50 may include or be in communication with a processor, computer, circuit or any other hardware component or ensemble of hardware components programmed with instructions for constructing, storing and displaying the images acquired by the imaging device 50. An integrated or separate display may be provided to allow the viewing of the resulting images by an operator or user of the spectroreflectometric system 20.

The spectral analyser 52 may be embodied by any suitable device allowing an analysis of light as a function of wavelength. The spectral analyser 52 may for example be embodied by an optical spectrometer. As known in the art, optical spectrometers typically decompose incoming light according to its spectrum, typically using light refraction (e.g. in a prism) or light diffraction (in a diffraction grating), and include a detector measuring the distributed intensity of the decomposed light. The spectral analyser 52 may include a computer or processor programmed with instructions to analyse the detected light spectrum in accordance with predetermined parameters, such as explained above. In some embodiments the spectral analyser 52 may be grating-based, as illustrated by way of example in FIG. 2. It will however be readily understood that a variety of other configurations and structural components may be used without departing from the scope of the present description. By way of example, the spectral analyser 52 may include at least one dispersive element such as grating in reflection or transmission or a prism.

The spectroreflectometric system 20 may further included an illumination light source 22 operable to generate an illumination light 24, which can be projected towards the fundus 30 of the patient's eye 21 in the acquisition mode. The illumination light source 22 may include one or more LED (Light Emitting Diode) emitters. The LED emitters of a given illumination light source 22 may have similar optical properties or different complementary optical properties selected in order to obtain the desired optical properties of the illumination light 24 once combined. It will be readily understood that numerous other variants of light sources such as lasers, OLEDs, fluorescent, incandescent, tungsten, and other light bulbs may be used in alternative embodiments. The expression "illumination light" is used herein to refer to electromagnetic radiation suitable for projection into the eye 21 of a patient and for inducing, producing or otherwise generating return light 32 which can yield information of interest on the fundus 30 of the patient's eye 21 upon suitable analysis. It will be readily understood that the term "light" is not considered limited to the visible portion of the electromagnetic spectrum. The illumination light 24 preferably has a broadband spectral profile encompassing all the wavelengths of interest for the spectral analysis which the system is configured to perform. In some variants, the illumination light may be white light. In other variants, the illumination light 24 may have a spectral profile designed in view of the field of use of the spectroreflectometric system 20. In yet another set of variants, the illumination light may have any other suitable spectral profile as dictated by one or more factors such as the optical properties of the patient's eye, the availability of light sources, the nature and characteristics of the spectral analysis to be performed, etc.

As mentioned above, the spectroreflectometric system 20 includes an optical assembly 26 defining on one hand, the imaging light path 34 between the patient's eye 21 and the imaging device 50 and, on the other hand, the spectral analysis light path 36 between the patient's eye 21 and the spectral analyser 52.

It will be readily understood that the optical assembly 26 may be embodied by a variety of configurations suitable to the purpose of illuminating a patient's eye and collecting the resulting return light. The optical assembly 26 may include one or more optical components configured to transfer the image of the fundus 30 onto an image plane 46. The optical components may include lenses, mirrors, polarizers, filters, etc. The optical components may be arranged in any suitable fashion as is generally known to those skilled in the art. The optical assembly 26 may further include other non-optical components such as mechanical or electrical components providing structural and/or functional support to the optical components such as fixed or displaceable mounts, screens, pinholes, step motors, etc.

The optical assembly 26 may include an illumination subassembly 28 optically coupled to the illumination light source 22 and configured to project the illumination light 24 from the illumination light source 22 towards the fundus 30 of the patient's eye 21.

In the illustrated configuration, the illumination subassembly 28 includes a holed mirror 38 positioned at an angle along the imaging light path 34. The holed mirror 38 has a central hole 39 aligned with the imaging light path 34. Preferably, the illumination light source 22 is positioned orthogonally to the eye of the patent 21, and the holed mirror makes a 45° angle with respect to the optical axis of the illumination light 24. In alternative embodiments, the illumination subassembly 28 may include one or more optical components having variable transmission and reflection properties, for example an mirror designed to have a low reflectivity in the enter and a high reflectivity around this center.

The illumination subassembly 28 further includes beam shaping optics projecting the illumination light 24 from the illumination light source 22 onto the holed mirror 38 for reflection towards the fundus of the patient's eye. The beam shaping optics includes one or more optical components interacting with the illumination light 24. In the illustrated embodiment, the beam shaping optics includes a first lens 40a, a second lens 40b and a third lens 40c successively disposed along the optical path between the illumination light source 22 to the holed mirror 38. A mask 42 is positioned between the second lens 40b and the third lens 40c. The mask 42 is optically aligned with the central hole 39 of the holed mirror 38 and is sized to block the center of the illumination beam 24. This configuration provides the illumination light 24 with an annulus shape so that it is reflected on the holed mirror 38. A screen 44 may be further provided between the first and second lenses 40a and 40b to prevent retroreflected light from the mask 42 from reaching the illumination light source 22. An output lens 41 and any other relevant optics may be provided between the holed mirror 38 and the eye of the patient 21.

In some implementations, an alignment light source 43 may optionally be provided optically coupled to the illumination subassembly 28 such that an alignment light beam generated therefrom can be launched into the same optical path as the illumination light. In some implementations, the alignment light source 43 may generate light in the near infrared spectral range to avoid discomfort to the patient.

It will be readily understood that the illumination subassembly 28 may be embodied by any suitable collection or optical components and accompanying structural, mechanical, electrical or other features collaborating to bring the illumination light from the illumination light source to the patient's eye with the desired optical characteristics. The components of the illumination subassembly may redirect, focus, collimate, filter or otherwise act on light in a variety of fashions. One skilled in the art will readily understand that a multitude of designs may provide such a result. For example, in some variants, one or more optical fibers may be used to carry the illumination light 24 at least partially from the illumination light source 22 towards the fundus 30. It will be further understood that the illumination light source 22 may be provided either separately or integrally to the optical assembly 26. In one example, the optical assembly 26 may include a light port configured to receive the illumination light directly or indirectly from the illumination light source.

Referring still to FIG. 2A, the optical assembly 26 further includes a beamsplitter 48, positioned along the imaging light path 34 and configured to direct an imaging portion 54 of the return light 32 to the imaging light path 34, and a spectral analysis portion 56 of the return light 32 to the spectral analysis light path 36. It will be readily understood that although in the illustrated variant the beamsplitter 48 is configured and arranged to transmit through the imaging portion 54 of the return light 32 and reflect the spectral analysis portion 56 of the return light 32, in other variants it may be configured and arranged to reflect the imaging portion 54 towards the imaging device 50, and transmit through the spectral analysis portion 56 towards the spectral analyser 52.

In some implementations, a focussing lens may be positioned between the holed mirror 38 and the beamsplitter 48. In some embodiments, the focussing lens may be mounted on a suitable translation actuator allowing its displacement along the imaging light path 34. Such a movement displaces the imaging plane 46 to compensate for refractive index variations in the eye of different patients. In other variants, the focussing lens may have a variable focus and may be adjustable by different means.

The imaging portion 54 of the return light 32 travels along the imaging light path 34 until it reaches the imaging device 50 for detection. Of course, numerous optical components could be provided along the imaging light path to collimate, focus, filter, redirect or otherwise affect the imaging portion 54 prior to reaching the imaging device 50. Beamshaping optics 51 are indicated as a blackbox representation of such components in the illustrated configuration of FIG. 2A.

The spectral analysis portion 56 of the return light 32 is deviated to the spectral analysis light path 36 and is eventually detected by the spectral analyser 54. The spectral analysis light path 36 is also optically coupled to the pointer light source 66 so that the pointer light beam 68 can counterpropagate along the spectral analysis light path 36 towards the beamsplitter 48. The operation of the pointer light source 66 and other features that may be provided along the spectral analysis light path 36 will be explained in further details below.

The beamsplitter 48 may operate according to any one of various principles to separate the light impinging thereon according to different portions. In one embodiment, the beamsplitter 48 is a dichroic beamsplitter. As well known in the art, dichroic optical components affect light according to its spectral characteristics. The dichroic beamsplitter 48 may have a spectral transmission profile tailored to the operation of the spectroreflectometric system 20. With additional reference to FIG. 3, in one example, the dichroic beamsplitter 48 has a transmission spectral profile defining:

two high transmissivity regions 60a, 60b, each having a 100% transmissivity ratio, which are associated with a spectrum for the imaging portion 54 of light travelling along the imaging light path. In other words, the portion of the return light having a wavelength within these regions will be allowed through the beamsplitter without deviation. In the illustrated example, the high transmissivity regions are lower than 500 nm and greater than 620 nm, respectively;

a low transmissivity region 62 associated with the spectrum of the spectral analysis portion 56 of the light 32 travelling along the imaging light path 34. In the illustrated example, the spectral analysis is preferably operated on light in the 500 nm to 620 nm range and the transmissivity of the beamsplitter 48 is null or negligible within this range, ensuring full reflection of this spectral component of the return light 32 to the spectral analysis light path 36; and a partial transmissivity region 64 associated with a spectrum of the pointer light beam 68. In the illustrated variant, the pointer light beam 68 has a wavelength in the red color range, for example at or near 635 nm. Light in the spectral range is partially transmitted and partially reflected by the beamsplitter, by way of example in a 50/50 ratio.

Figure 3:
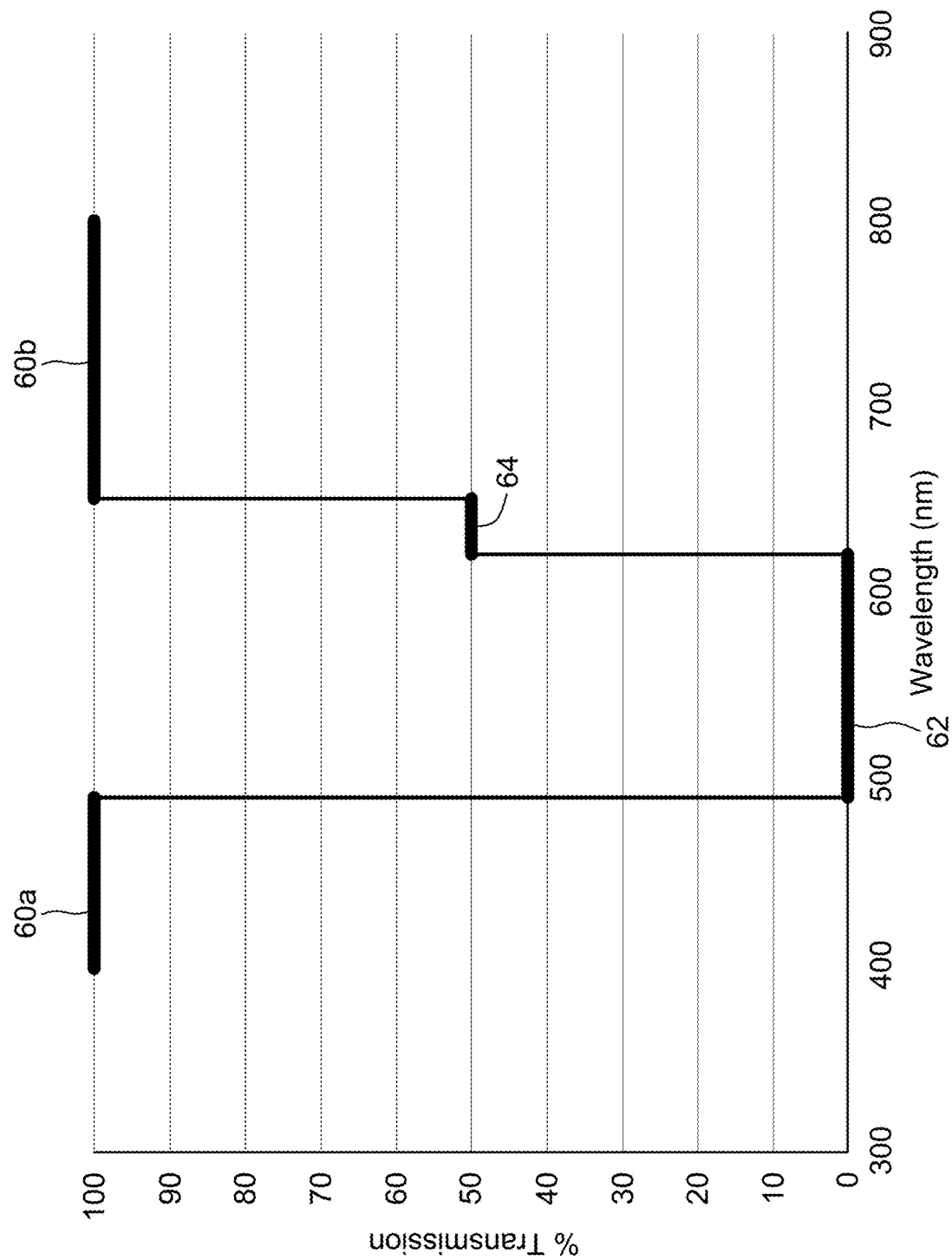
FIG. 3 is a graph of the transmission profile of a dichroic beamsplitter for use in a system according to one example of implementation.

As one skilled in the art will readily understand, the graph of FIG. 3 illustrates an ideal spectral profile and practical implementations may only approximate such an ideal variation.

In other embodiments, the beamsplitter 48 may separate light according to other characteristics than its spectral contents. The beamsplitter 48 may for example be configured to divide the return light 32 travelling along the imaging light path 34 into the imaging portion and the spectral analysis portion according to intensity ratios independently of the light's wavelength or polarization state. In other variants, the beamsplitter 48 may be configured to divide the return light 32 travelling along the imaging light path 34 into the imaging portion and the spectral analysis portion according to polarisation directions.

Referring back to FIG. 2A, in some implementations, the optical assembly 26 includes first and second optical fiber links 70 and 72. The first optical fiber link 70 extends between the spectral analysis light path 34 and the spectral analyser 52. The second optical fiber link 72 extends between the spectral analysis light path 34 and the pointer light source 66. The optical assembly 26 further includes a three-prong coupler 74 optically coupling the spectral analysis light path 34, the first optical fiber link 70 and the second optical fiber link 72.

Figure 4C:
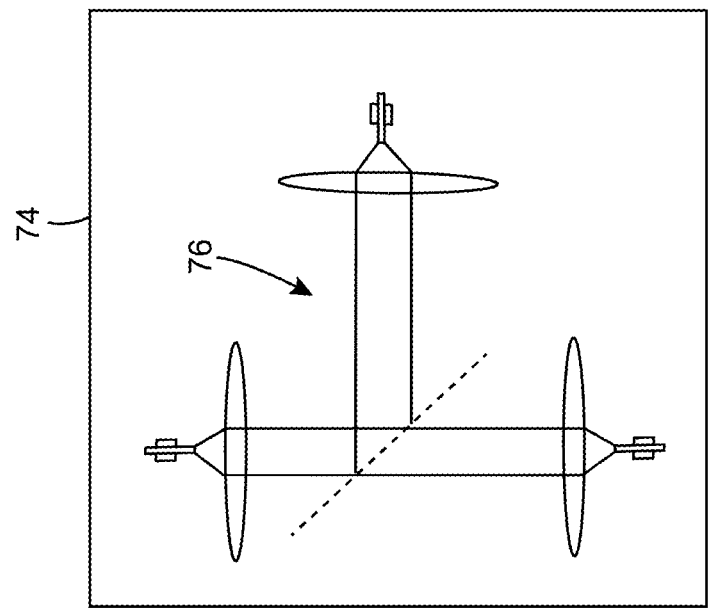
FIGS. 4A to 4C show different configurations of a three-prong coupler for use in a system according to some embodiments.
Figure 4B:
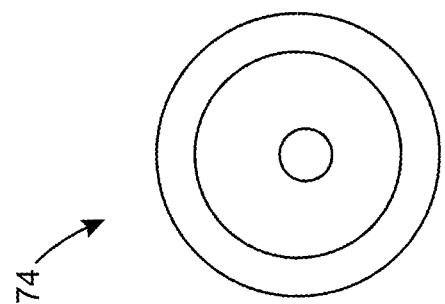
Figure 4A:
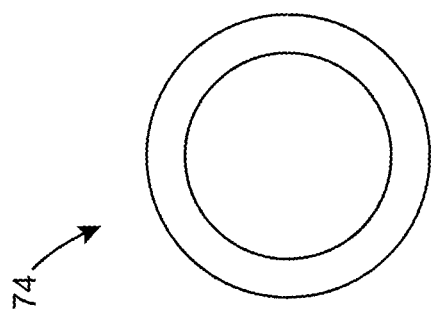

The three-prong coupler 74 may be embodied by various devices and/or configurations providing light circulation from the spectral analysis light path 36 to the first optical fiber link 70, allowing the spectral analysis portion 56 of the return light 32 to reach the spectral analyser 52, and from the second optical fiber link 72 to the spectral analysis path 36, allowing the pointer light beam 68 to be launched in the system towards the eye of the patient 21. Referring to FIGS. 4A to 4C, different variants of the three-prong coupler 74 are illustrated. In the example of FIG. 4A, the three-prong coupler 74 includes a multimode optical circulator. FIG. 4B shows another variant where the three-prong coupler 74 comprises a double-clad optical fiber, which may support the propagation of the pointer light beam in the core, and the light collection for spectral analysis region through the cladding sent to the spectral analyser. In this case, the core mode is optically coupled to the first optical fiber link, and the cladding mode is optically coupled to the second optical fiber link (or vice versa). In yet another variant, the three-prong coupler 74 may be a free-space configuration, for example based on a free-space beamsplitting configuration 76.

Of course, numerous optical components could be provided along the spectral analysis light path to collimate, focus, filter, redirect or otherwise affect the imaging portion 54 prior to reaching the three-prong coupler 74. Beamshaping optics 78 are indicated as a blackbox representation of such components in the illustrated configuration of FIG. 2A. By way of example, a lens 79 focussing light onto the three-prong coupler is also illustrated.

The pointer light source 66 may be embodied by any light source generating a pointer light beam 68 suitable for pointing functionalities. In one example, the pointer light source 66 may be a laser diode. The pointer light beam 68 may have any wavelength or spectral contents safe for the eye of the patient and within the detection range of the imaging device. The pointer light source may for example emit in the visible or near infrared spectral ranges.

In accordance with some implementations, the spectroreflectometric system 20 includes a controller 80. The controller 80 is configured to operate in the acquisition mode and in the pointer mode. In some implementations, the acquisition mode and pointer mode may be operated alternatively, whereas in other implementations they may be operated concurrently. In the acquisition mode, the controller 80 operates the illumination light source 22, the imaging device 50 and the spectral analyser 52 to concurrently obtain an image of the fundus 30 of the patient's eye 21 and a spectral analysis of an analysis spot on this fundus 30. In the pointer mode, the controller 80 operates the pointer light source 66 and the imaging device 50 to obtain a visual representation of the analysis spot within the image obtained in the acquisition mode.

Referring to FIGS. 5A to 5C, examples of the results obtained through an implementation of the method and system described herein is described. FIG. 5A shows the visual representation of an analysis spot 82 obtained in the pointer mode, where the pointer light beam from the pointer light source is optically guided through the system to reach the fundus of the patient's eye. The obtained visual representation is an image of this point source onto the sensor of the imaging device. This image may be used as a "laser pointer" to define the area for which the spectral analysis is performed, since both optical fiber links 70 and 72 share the same output at the three-prong coupler 74. FIG. 5B shows the image 84 of the fundus and the spectral analysis 85 of the analysis spot defined by the pointer jointly obtained in acquisition mode. Preferably, the controller includes precise synchronisation electronically enabling the successive operation of the system in the pointer mode and acquisition mode. In some embodiments, the image and spectral analysis information shown in FIG. 5B may be obtained prior to the visual representation of the analysis spot shown in FIG. 5A. Optionally, the position of the analysis spot obtained in pointer mode may be superimposed on the image of the retina obtained in acquisition mode, as shown in FIG. 5C. An oxygen concentration from the corresponding region may be jointly provided in oximetry applications.

FIG. 6A shows a timing diagraph for control signals provided from the controller to the illumination light source 22, the imaging device 50, the spectral analyser 52 and the pointer light source 66, respectively. In the pointer mode $P_m$, the pointer light source 66 and the imaging device 50 are turned on to obtain a visual representation of the analysis spot within the image, such as shown in FIG. 5A. Both the illumination source 22 and the spectral analyser 52 are turned off. In the acquisition mode $A_m$, the illumination source 22, the imaging device 50 and the spectral analyser 52 are turned on, whereas the pointer light source 66 is turned off. As a result, an image of the fundus of the eye is acquired by the imaging device and a spectral analysis of the analysis spot is also obtained from the spectral analyser, such as shown in FIG. 5B.

In some implementations, it may be advantageous to operate the illumination light source in a continuous fashion. Such an operation may prevent the subject perceiving a flicker of light during the acquisition. Referring to FIG. 6B, there is shown an alternative timing diagram. In this variant, the illumination light source 22, the imaging device 50 and the pointer light source 66 remain turned on, while the spectral analyser 52 is turned on for the acquisition mode $A_m$ and off for the pointer mode $P_m$. By operating the illumination light source continually and without interruptions in the transitions between the acquisition mode and pointer mode, flickering effects perceivable by the patient can be avoided. It is noted that in the example of FIG. 6B the control signal for the imaging device 50 is shown as an AC signal, whereas in the example of FIG. 6A, a DC signal is used.

In the variant of FIG. 6B it may be desirable to provide an image of the eye fundus without the superimposed spot from the pointer light beam. This may be accomplished in a variety of manners. In one implementation, the pointer light source may be turned off during the acquisition mode. In another variant, post-processing may be performed on the acquired image to remove the pointer light source from the image. In yet another variant, a second camera may be provided in the imaging path passed the dichroic beamsplitter, and a second beamsplitter may be provided, spectrally dividing the return light to send the image of the fundus to one of the camera and the image of the pointer source to the other. Optionally, in implementations where the pointer light source 66 remains on, an optical filter blocking light at the wavelength of the pointer light beam from the pointer light source may be provided in the spectral analysis path, upstream of the spectral analyser. It is to be noted that the presence of the optical filter may remove spectral contents from the light reaching the spectral analyser, but that such a removal may not impact the results of the spectral analysis in cases where the optical filter is designed to block wavelengths outside of a spectral region of interest for such an analysis. The wavelength of the pointer light source may be selected accordingly. By way of example, in the context of oxyhemoglobin and deoxyhemoglobin evaluation such as shown in FIG. 5B, blue light, typically in a wavelength range of the order of 450 nm to 490 nm, could be used and filtered from the signal reaching the spectral analyser without interfering with the spectral analysis.

The spectroreflectometric system 20 may include additional components and functionalities.

Figure 7A:
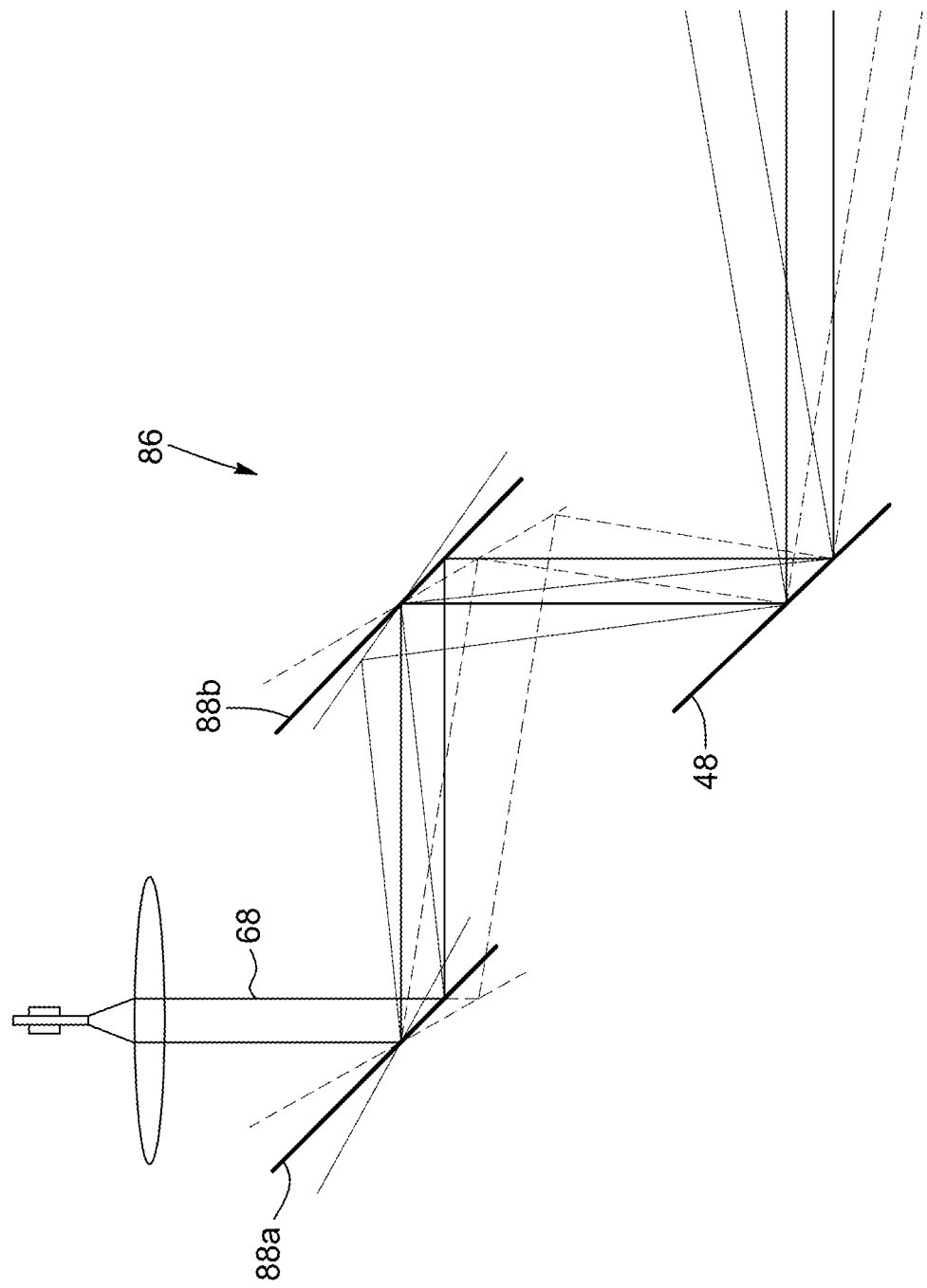
FIGS. 7A and 7B are examples of configuration for a spot shifting mechanism for use in a spectroreflectometric system according to one embodiment.
Figure 7B:
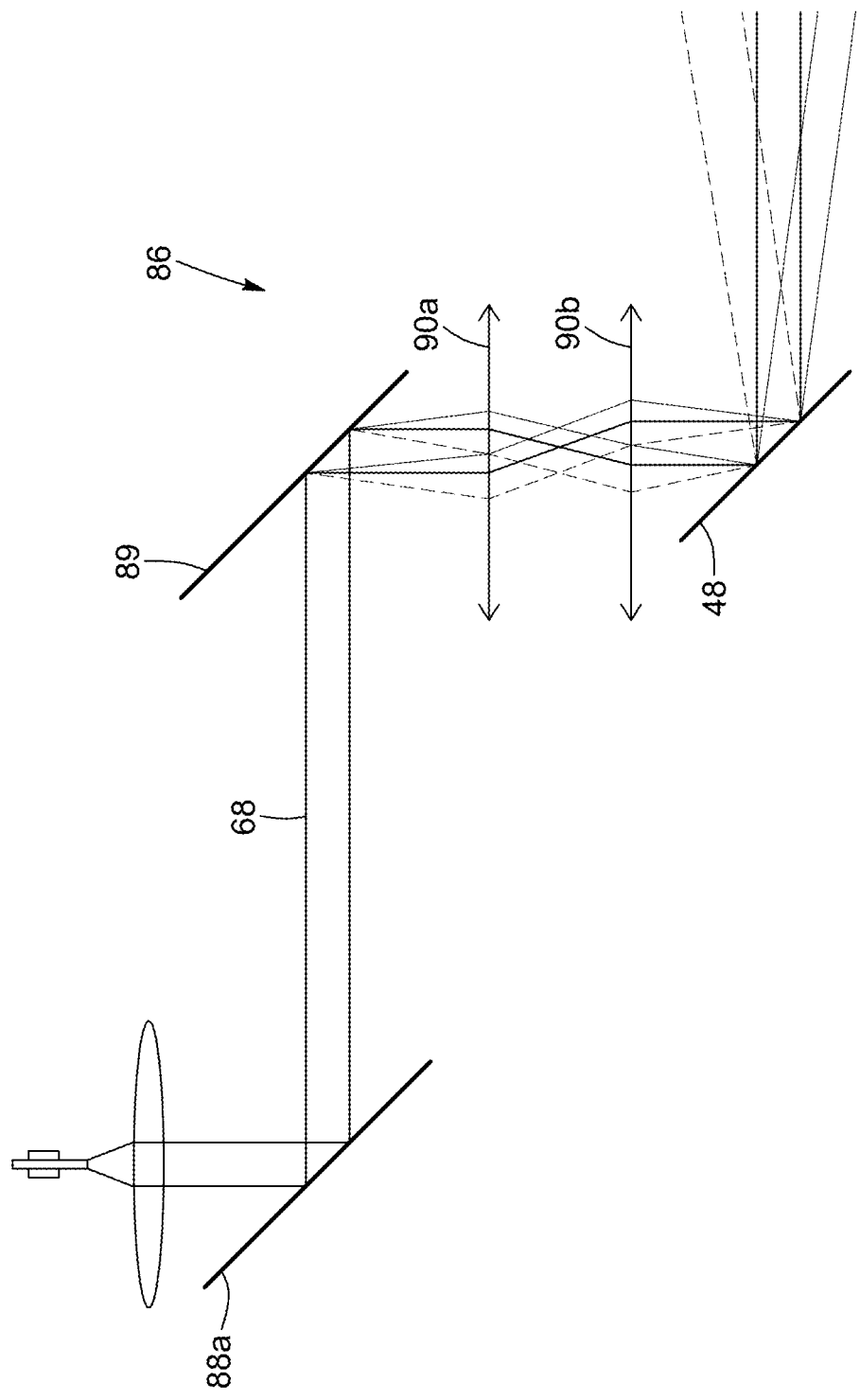

Referring back to FIG. 2A, in some implementations, the spectroreflectometric system 20 may include a spot shifting mechanism 86 positioned in the spectral analysis path 36 and configured to shift the position of the analysis spot over the fundus 30 of the patient's eye without impact on the imaging portion 21. The spot shifting mechanism 86 may include shift optics such as one or more steerable mirrors. A pivoting of the steerable mirrors can be used to change the incidence angle between the pointer light beam 68 travelling along the spectral imaging light path 36 and the beamsplitter 48. Referring to FIGS. 7A and 7B, two examples of configurations of the spot shifting mechanism are shown. On FIG. 7A, first and second mirrors 88a, 88b with displacement both in phi and theta direction are used to change the angle of incidence of the pointer light beam 68 onto the beamsplitter 48. The direction of displacement of the first mirror 88a must be opposite to the one of the second mirror 88b in order to keep the position of the pointer light beam 68 on the beamsplitter 48 and to only change the angle of incidence. In FIG. 7B, a gimbal mirror 89 is used in place of the second mirror 88b. This scheme, used jointly with two lenses 90a and 90b used in 4f configuration, enables the variation of the angle of incidence of the pointer light beam 68 onto the beamsplitter 48 without changing the position at which the pointer light beam 68 hits the beamsplitter.

Figure 2B:
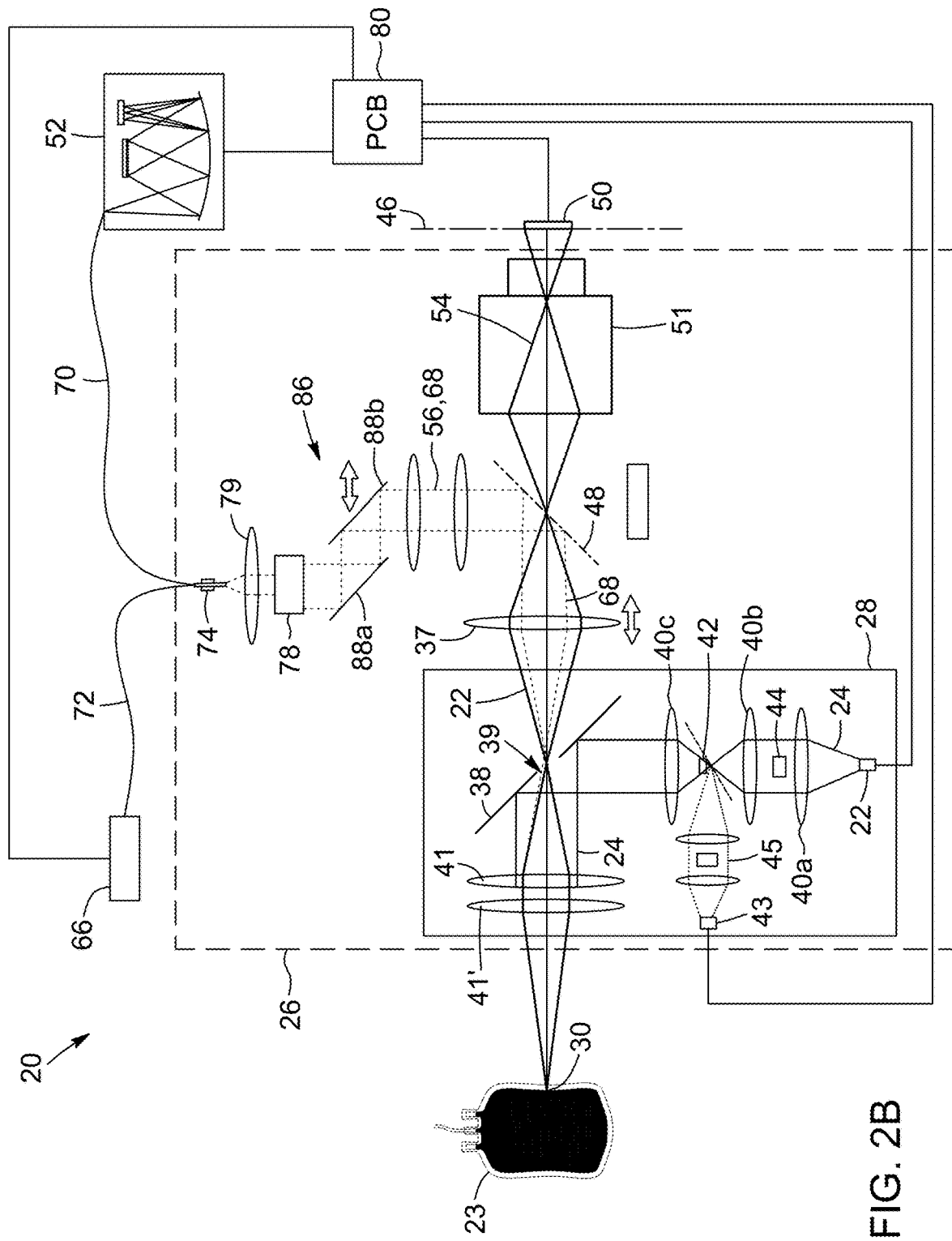
FIG. 2B is a detailed representation of a spectroreflectometric system according to one example of implementation, for use to perform a spectral analysis of a blood sample.

Referring to FIG. 2B, there is shown a variant of the spectroreflectometric system 20 similar to the one described above, for use in performing a spectral analysis on a medium other than the fundus of the eye. By way of example, in the illustration of FIG. 2B the medium under study is a pocket of liquid 23 (for example containing blood or plasma).

The spectroreflectometric system of FIG. 2B includes all the same components as the system shown in FIG. 2A, including the optical assembly 26 and illumination subassembly 28. In this variant, the illumination subassembly 28 further includes an additional output lens 41'. The additional output lens 41' can be added to the configuration of FIG. 2A to provide focalization and form an image of the medium being probed on the imaging device 50. As one skilled in the art will readily understand, this approach can provide an easy adaptation of a system initially conceived to probe the fundus of the eye, since such a conception considers the natural light focalisation performed by the lens of the eye, which is in essence replaced by the additional output lens 41'. In other variants, the output lens 41 and additional output lens 41' may be replaced by a single lens or different optical arrangement.

Of course, numerous modifications could be made to the embodiments described above without departing from the scope of the invention as described in the appended claims.

The invention claimed is:

1. A system for performing a spectral analysis on a medium, comprising:
   an imaging device;
   a spectral analyser;
   an optical assembly defining an imaging light path between the medium and the imaging device and a spectral analysis light path between the medium and the spectral analyser, the optical assembly comprising a beamsplitter positioned along the imaging light path and configured to direct an imaging portion of light travelling along the imaging light path to the imaging device and a spectral analysis portion of said light to the spectral analysis light path;
   a pointer light source optically coupled to the spectral analysis light path and operable to generate a pointer light beam; and
   a controller configured to operate in:
      an acquisition mode wherein the controller operates the imaging device and the spectral analyser to concurrently obtain an image of the medium and a spectral analysis of an analysis spot in said medium; and
      a pointer mode wherein the controller operates the pointer light source and imaging device to obtain a visual representation of the analysis spot within said image.

2. The system according to claim 1, wherein the beamsplitter is a dichroic beamsplitter.

3. The system according to claim 1, wherein the beamsplitter is configured to divide the light travelling along the imaging light path into the imaging portion and the spectral analysis portion according to intensity ratios.

4. The system according to claim 1, wherein the beamsplitter is configured to divide the light travelling along the imaging light path into the imaging portion and the spectral analysis portion according to polarisation directions.

5. The system according to claim 1, wherein the optical assembly comprises:
   a first optical fiber link extending between the spectral analysis light path and the spectral analyser;
   a second optical fiber link extending between the spectral analysis light path and the pointer light source; and
   a three-prong coupler optically coupling the spectral analysis light path, the first optical fiber link and the second optical fiber link.

6. The system according to claim 1, wherein the optical assembly comprises an illumination subassembly configured to project illumination light towards the medium, said system further comprising an illumination light source operable to generate the illumination light and optically coupled to the illumination subassembly.

7. The system according to claim 1, wherein the controller is configured to:

in the acquisition mode, turn on the imaging device, the illumination light source and the spectral analyser and turn off the pointer light source; and in the pointer mode, turn on the pointer light source and the imaging device, and turn off the illumination light source and the spectral analyser.

8. The system according to claim 1, wherein the controller is configured to operate the illumination light source continuously.

9. The system according to claim 1, further comprising a spot shifting mechanism positioned in the spectral analysis light path and configured to shift a position of the analysis spot over said medium.

10. A spectroreflectometric system for performing a spectral analysis on the fundus of a patient's eye, comprising:
   an imaging device;
   a spectral analyser;
   an optical assembly defining an imaging light path between the patient's eye and the imaging device and a spectral analysis light path between the patient's eye and the spectral analyser; and
a pointer light source operable to generate a pointer light beam and optically coupled to the spectral analysis light path such that said pointer light beam is projectable on the fundus of the patient's eye at an analysis spot of said spectral analyser.

11. A spectroreflectometric system according to claim 10, wherein the optical assembly comprises a beamsplitter positioned along the imaging light path and configured to direct an imaging portion of light travelling along the imaging light path to the imaging device and a spectral analysis portion of said light to the spectral analysis light path.

12. The spectroreflectometric system according to claim 11, wherein the beamsplitter is configured to divide the light travelling along the imaging light path into the imaging portion and the spectral analysis portion according to intensity ratios or to polarisation directions.

13. The spectroreflectometric system according to claim 10, wherein the optical assembly comprises:
   a first optical fiber link extending between the spectral analysis light path and the spectral analyser;
   a second optical fiber link extending between the spectral analysis light path and the pointer light source; and
   a three-prong coupler optically coupling the spectral analysis light path, the first optical fiber link and the second optical fiber link, said the three-prong coupler comprising one of a multimode optical circulator, a double-clad optical fiber and a free-space beamsplitting configuration.

14. The spectroreflectometric system according to claim 10, wherein the optical assembly comprises an illumination subassembly configured to project illumination light towards the fundus of the patient's eye.

15. The spectroreflectometric system according to claim 14, further comprising an illumination light source operable to generate the illumination light and optically coupled to the illumination subassembly.

16. The spectroreflectometric system according to claim 15, further comprising a controller configured to operate in:
   an acquisition mode wherein the controller operates the imaging device and spectral analyser to concurrently obtain an image of the fundus of the patient's eye and a spectral analysis of the analysis spot on said fundus; and
   a pointer mode wherein the controller operates the pointer light source and imaging device to obtain a visual representation of the analysis spot within said image.

17. The spectroreflectometric system according to claim 16, wherein the controller is configured to:
   in the acquisition mode, turn on the imaging device, the illumination light source and the spectral analyser and turn off the pointer light source; and
   in the pointer mode, turn on the pointer light source and the imaging device, and turn off the illumination light source and the spectral analyser.

18. The spectroreflectometric system according to claim 16, wherein the controller is configured to operate the illumination light source continuously.

19. The spectroreflectometric system according to claim 10, further comprising a spot shifting mechanism positioned in the spectral analysis light path and configured to shift a position of the analysis spot over said fundus of the patient's eye.

20. A spectroreflectometric method for performing a spectral analysis on the fundus of a patient's eye, comprising:
   providing a spectroreflectometric system operable in an acquisition mode and a pointer mode;
   in the acquisition mode:
      illuminating the fundus of the patient's eye, thereby obtaining return light from said fundus, the return light propagating along an imaging light path;
      separating the return light into an imaging portion continuing along the imaging light path, and a spectral analysis portion diverted to a spectral analysis light path;
      detecting the imaging portion using an imaging device to obtain an image of the fundus of the patient's eye;
      detecting the spectral analysis portion using a spectral analyser to obtain and a spectral analysis of an analysis spot on said fundus;
   in the pointer mode:
      coupling a pointer light beam to the spectral analysis light path so that said pointer light beam is projected towards the fundus of the patient's eye and a reflection thereof propagated along the imaging light path to the imaging device;
      detecting the reflection of the pointer light beam using the imaging device to obtain a visual representation of the analysis spot within said image.

* * * * *